United States Patent [19]

Sielcken et al.

[11] Patent Number: 5,495,041
[45] Date of Patent: Feb. 27, 1996

[54] PROCESS FOR THE PREPARATION OF A PENTENOATE ESTER

[75] Inventors: Otto E. Sielcken, Sittard; Frank P. W. Agterberg, Susteren; Nicolaas F. Haasen, Sittard, all of Netherlands

[73] Assignees: DSM N.W., Heerlen, Netherlands; E. I. Du Pont de Nemours and Company, Wilmington, Del.

[21] Appl. No.: 395,601

[22] Filed: Feb. 22, 1995

[51] Int. Cl.$^6$ .................................................. C07C 51/14
[52] U.S. Cl. .................................................. 560/207
[58] Field of Search ............................................ 560/207

[56] References Cited

U.S. PATENT DOCUMENTS 4,739,110  4/1988  Drent ........................ 560/207
5,026,901  6/1991  D'Amore ..................... 560/207
5,028,734  7/1991  Drent ........................ 560/207
5,149,868  9/1992  Drent ........................ 560/207

FOREIGN PATENT DOCUMENTS 235864  9/1987  European Pat. Off. .
284170  9/1988  European Pat. Off. .
495547  7/1992  European Pat. Off. .

Primary Examiner—Paul J. Killos
Attorney, Agent, or Firm—Cushman Darby & Cushman

[57] ABSTRACT

A process is described for the preparation of a pentenoate ester by carbonylation of butadiene or butadiene derivate in the presence of carbon monoxide, a alcohol and a catalyst system comprising palladium, an carboxylic acid and a phosphine ligand, wherein the carboxylic acid is pentenoic acid.

9 Claims, No Drawings

PROCESS FOR THE PREPARATION OF A PENTENOATE ESTER

The invention relates to a process for the preparation of a pentenoate ester by carbonylation of butadiene or butadiene derivative in the presence of carbon monoxide, an alcohol and a catalyst system comprising palladium, a carboxylic acid and a phosphine ligand.

A carbonylation reaction means every reaction between a nonsaturated substrate, a hydroxy group containing reactant and carbon monoxide.

U.S. Pat. No. 5,028,734 describes a process in which the carbonylation of butadiene is performed with a catalyst system comprising palladium, a substituted or unsubstituted benzoic acid and a multidentate phosphine ligand, such as 1,4-bis(diphenylphosphino)butane.

A disadvantage of the process of U.S. Pat. No. 5,028,734 is that the catalytically active carboxylic acid reacts with the alcohol to form the corresponding, catalytically inactive, ester. The loss of the acid co-catalyst is disadvantageous because the overall catalyst activity will then decrease and a lower selectivity to pentenoate ester will result. In, for example, a continuous process it is important that the catalyst activity remains at a certain higher level over a longer period of time. In order to keep the catalyst system of U.S. Pat. No. 5,028,734 active, fresh carboxylic acid must be added to the reaction system which results in a high consumption of carboxylic acid. Substituted benzoic acid, which acid according to U.S. Pat. No. 5,028,734 preferably used as the carboxylic acid, is not easily available and therefore expensive. The need to add fresh substituted benzoic acid will make this process economically unattractive for a commercial large scale plant.

An object of the present invention is to provide an economically attractive process for the preparation of pentenoate ester by carbonylation of butadiene.

This object of the invention is achieved in that the carboxylic acid is pentenoic acid.

It has been discovered that when pentenoic acid is used as the acid co-catalyst the catalyst activity is comparable to when substituted benzoic acid is used. Advantageously when only pentenoic acid is used as the carboxylic acid, it reacts with the alcohol and the product of the present process (the pentenoate ester) will be formed. Therefore no extra side products, such as, for example a benzoate ester as in the process of U.S. Pat. No. 5,028,734, will be formed in the reaction mixture. This is advantageous because, for example, the separation of the various components in the resulting reaction mixture can be performed more simply.

Another advantage is that fresh pentenoic acid which is needed to compensate the pentenoic acid lost during the carbonylation can be easily obtained, for example, by hydrolysis of the pentenoate ester in a separate step. This manner of obtaining fresh carboxylic acid by hydrolysis of the ester formed is also possible when using the state of the art acids as described in U.S. Pat. No. 5,028,734. The advantage of using pentenoic acid is, however, that the ester which is to be hydrolysed need not be isolated from the pentenoate ester as would be the situation with, for example, a benzoate ester. Therefore a process using pentenoic acid can be performed in an economically attractive manner.

Furthermore, it has been discovered that by adding small amounts of water, fresh pentenoic acid as described above does not have to be supplied. This will be described below in more detail.

The term butadiene derivatives means those compounds which yield pentenoate ester or pentenoic acid as the major product when carbonylated in the process according to the invention. If no statement is made to the contrary, all references to butadiene shall also include butadiene derivatives in this description. It is also possible to carbonylate mixtures of butadiene and butadiene derivatives with the process according to the invention. Although butadiene derivatives can be readily carbonylated in the present process, butadiene is preferred because of its availability. The butadiene can be used in pure form, or in admixture with aliphatic compounds. An exemplary such admixture is the $C_4$-cut obtained in a steam cracker process. Such a $C_4$-cut can comprise butadiene plus 1-butene, 2-butene, and/or isomeric butynes.

Preferred butadiene derivatives are represented by the following general formulae:

$$CH_3—CH=CH—CH_2—X \quad (1)$$

$$CH_3—CHX—CH=CH_2 \quad (2)$$

wherein X represents an organic group with 1 to 20 carbon atoms or an inorganic group. Examples of suitable organic groups are $—OR^4$ or $—OC(O)R^5$ groups, in which $R^4$ and $R^5$ can be, for example, a $C_1$–$C_6$ alkyl, $C_2$–$C_6$ alkenyl, $C_6$–$C_{14}$ aryl $C_7$–$C_{14}$ aralkyl or $C_7$–$C_{14}$ alkaryl group. Examples of these groups are methyl, ethyl, n-propyl, iso-propyl, n-butyl, tert-butyl, pentyl, cyclopentyl, cyclohexyl, hexyl, propenyl, butenyl, pentenyl, phenyl, naphthyl, benzyl, tosyl. Examples of other suitable organic groups or inorganic groups are $—OH$, $—PO_4$, $—PR^6R^7$, $—NH—CO—R^8$, $—NH_2$, and $SR^9$, in which $R^6$, $R^7$, $R^8$ and $R^9$ can be the same as defined above for $R^4$ and $R^5$.

Butadiene derivatives include, for instance, 1-methoxy 2-butene, 3-methoxy 1-butene, 1-ethoxy 2-butene, 3-ethoxy 1-butene, isomeric butenylpentenaoate, 1-butene 3-carbonate, 2-butene 1-carbonate, 3-hydroxy 1-butene, and 1-hydroxy 2-butene. Methods of making alkoxy butenes, e.g. methoxy butene, are described in U.S. Pat. Nos. 4,343,120 and 4,590,300, the complete disclosures of which are incorporated herein by reference.

The phosphine ligand used in the process according the invention can be a monodentate or multidentate phosphine ligand, or a mixture thereof.

When a monodentate phosphine ligand is used the reaction is preferably performed continuously or semi-continuously wherein the amounts of the reactants are substantially maintained during the whole process such that the molar ratio of butadiene to palladium in the reaction mixture is less than 70:1, the molar ratio of carboxylic acid to palladium is greater than 10:1, and the molar ratio of alcohol or water to butadiene is less than 2:1. Preferably the butadiene/palladium ratio is greater than 1:1 and more preferably it is higher than 2:1. It has been found that a high selectivity to pentenoate ester can be obtained when the carbonylation is performed in the above described manner.

To achieve such low butadiene/palladium ratios the butadiene is preferably continuously supplied to the carbonylation reaction at a rate of at most 150 mol butadiene per hour per mol palladium present during the carbonylation. More preferably this rate is less than 80 mol butadiene per hour per mol palladium at a temperature of the carbonylation below 160° C.

The amounts of reactants specified herein above should preferably be maintained substantially during the whole process. By preference, the term substantially during the whole process means more than 90% of the process as expressed in residence time.

An additional advantage of the use of monodentate phosphine ligands is that the amount of 2-pentenoate ester in the pentenoate ester mixture formed is lower than when bidentate phosphine ligands, such as described in U.S. Pat. No. 5,028,734, are used in the process according to the invention. A "low amount" means an amount of less than 10% 2-pentenoate ester relative to the total amount of pentenoate esters. This is advantageous when such a mixture is used in the hydroformylation of pentenoate ester to the terminal 5-formylvalerate ester with a rhodium-based catalyst system, such as described, for example, in U.S. Pat. No. 5,264,616, the complete disclosure of which is incorporated herein by reference. The 2-petenoate ester in the mixture has an adverse effect on the selectivity to 5-formylvalerate ester as is clear from U.S. Pat. No. 5,264,616.

The monodentate phosphine ligand is preferably a compound represented by to the following general formula (3):

wherein $R^1$, $R^2$ and $R^3$ each individually represent an optionally substituted organic group. This organic group can be a $C_1$–$C_{20}$ alkyl group, a $C_2$–$C_{20}$ alkenyl group, a $C_6$–$C_{18}$ aryl group or a cyclic group with 4–12 carbon atoms in which the ring of the cyclic group also contain one or more heteroatoms, for example nitrogen. Alkyl groups include, among others, methyl, ethyl, isopropyl, tert-butyl, cyclohexyl or cyclooctyl. An exemplary alkenyl group is butenyl. Exemplary cyclic groups containing heteroatoms include, among others, 6-methyl-2-pyridyl and 4,6-dimethyl-2-pyridyl. By preference, at least one of the organic groups $R^1$, $R^2$ and $R^3$ is a $C_6$–$C_{16}$ aryl group and more preferably a $C_6$–$C_{14}$ aryl group. Aryl groups include, for instance, naphtyl, phenyl, benzyl, cumenyl, mesityl, tolyl and xylyl. The organic group can be substituted, for example, with halogen atoms, for example Cl, Br or F, $C_1$–$C_6$ alkyl, $C_6$–$C_{18}$ aryl, $C_1$–$C_6$ alkoxy, carboxy, carbalkoxy, acyl, trihalogenmethyl, cyano, dialkylamino, sulphonylalkyl or alkanoyloxy groups. Substituents can be groups with electron withdrawing or electron donating properties.

Monodentate phosphine ligands include, for instance, tri-p-tolylphosphine, tri-p-methoxyphenyl phosphine, diphenylpentylphosphine or dimethylphenylphosphine. Preferably triphenylphosphine is used because this compound is readily available.

To simplify the process, by preference no other carboxylic acids besides pentenoic acid are present. Other carboxylic acids can react with the alcohol to form their ester products, which would complicate further processing. Fresh pentenoic acid needed to replace the lost acid of the catalyst system can advantageously be prepared in a separate step by hydrolyzing a portion of the pentenoate ester formed in the carbonylation to the pentenoic acid. The pentenoic acid thus obtained can be used in a following carbonylation in which the catalyst system of the previous carbonylation is reused.

Such a separate hydrolysis can, for example, be performed by contacting some of the pentenoate ester with an acid ion exchange resin in the presence of water. Such contacting can be performed in, for example, an on-purpose unit operation (specific designed process step or equipment) or in one of the distillation columns used for separating the pentenoate ester from one of the other components of the reaction mixture leaving the reactor.

It has been found that the addition of water to the carbonylation reaction will result in a stable concentration of pentenoic acid in a continuous process. The amount of water should be sufficient to maintain a catalytically active level of pentenoic acid during the carbonylation. The amount of water needed will depend on the amount of pentenoic acid being consumed by esterification during the carbonylation. The rate of esterification will depend on the reaction conditions, selected and can be easily determined by analyzing the reaction mixture leaving the reactor.

Preferred multidentate phosphine ligands can are represented by the following general formula

wherein is 2–6, $R^5$ is a multivalent (valency equals n) organic bridging group with 2 to 20 carbon atoms and $R^4$ and $R^6$ each individually represent an optionally substituted organic group. By preference, n is 2 in formula (4). Organic groups for $R^4$ and $R^6$ are the same as described for $R^1$, $R^2$ and $R^3$. The substituents for the organic groups in formula (4) are the same as described for the monodentate phosphine ligands.

Divalent organic bridging groups include $C_2$–$C_{10}$ alkylidene groups, for example ethylene, trimethylene, tetramethylene, pentamethylene or trans-1,2-cyclobutene; and $C_6$–$C_{20}$ divalent arylene groups such as, for example, dinaphytyl or diphenyl.

The bidentate phosphine ligands include, among others, 1,3-bis(diphenylphosphino)propane, 1,4-bis(diphenylphosphino)butane, 2,3-dimethyl-1,4-bis(diphenylphosphino)butane, 1,4-bis(dicyclohexylphosphino)butane, 1,3-bis(di-p-tolylphosphino)propane, 1,4-bis(di-p-methoxyphenylphosphino)butane, 2,3bis(diphenylphosphino)-2-butene, 1,3-bis(diphenylphosphino)- 2-oxopropane, 2-methyl-2-(methyldiphenylphosphino)- 1,3 -bis(diphenylphosphino)propane, 2,2'-bis(diphenylphosphino)biphenyl, 2,3-bis(diphenylphosphino)naphthalene, 1,2-bis(diphenylphosphino)cyclohexane, 2,2-dimethyl-4,5-bis(diphenylphosphino)dioxolane, 2,3-o-isopropylidene-2,3-dihydroxy-1,4-bis(diphenylphosphino)-butane(DIOP), trans-1,2-bis(di(m-methylphenyl)phosphinemethyl)cyclobutane, trans[(bicyclo[ 2.2.1]-heptane-2,3-diyl)bis(methylene)]bis[diphenylphosphine], trans-[(bicyclo[2.2.2]octane-2,3-diyl)bis(methylene)]-bis[diphenylphosphine], trans-1,2-bis(diphenylphosphino-methyl)cyclobutane (DPMCB), trans-1,2-bis(diphenyl-phosphinemethyl)trans-3,4-bis(phenyl)cyclobutane and 2,2'-bis(diphenylphosphino)- 1,1'-binapthyl (BINAP).

If a low amount of 2-pentenoate ester in the pentenoate ester mixture is desired, as described above, a divalent bis(n-cyclopentadienyl) coordination group of a transition metal is preferably used as a bridging group $R^5$. The transition metal can be selected from among Fe, Zr, Co, Ni, Ti, Ru and W. Preferably Fe is used, in which case the bridging group is referred to as a ferrocenyl group.

Bidentate phosphine ligands with a ferrocenyl bridging group include, for instance, 1,1'-bis(diphenyl-phosphine)ferrocene, 1,1'-bis(diisobutyl-phosphino) ferrocene, 1,1'-bis-(diisopropylphosphino)-ferrocene, 1,1'-bis(dicyclohexylphosphino)-ferrocene, 1,1'-bis(isopropylcyclohexylphosphino)-ferrocene, 1,1'-bis(di-t-butylphosphino)ferrocene, 1-(diisopropylphosphine)-1'-(phenylisopropylphosphino)-ferrocene, 1-(diphenylphosphino)- 1'-(diisopropyl-phosphino)ferrocene, 1,1'-bis(isopropylphenylphosphino)-ferrocene.

The molar ratio of phosphine ligand to palladium depends on the specific phosphine ligand used in the process according to the invention. This ratio will preferably be between 1:1 and 20:1. For multidentate phosphine ligands this ratio is preferably between 1:1 and 10:1. When using monodentate phosphine ligands this ratio is preferably greater than 5:1. When this ratio is too high the catalytic effect of the catalyst system is weaker and by-products such as vinyl cyclohexene and high-molecular products may form. Both multidentate and monodentate phosphine ligands can be simultaneously present during the carbonylation.

All inert solvents are in principle suitable as an additional solvent, although it is also possible to use an excess of one of the reactants or (by) products in such an amount that a suitable liquid phase is formed. Examples of (by) products are the pentenoate esters, $C_9$-esters and high boiling by-products. The pentenoic acid can also be used as solvent. Examples of inert solvents are sulphoxides and sulphones, such as for instance, dimethyl sulphoxide, diisopropyl sulphone; aromatic solvents, such as benzene, toluene, xylene; esters, such as methyl acetate, methyl valerate, pentenoate esters and butyrolactone; ketones, such as acetone or methylisobutyl ketone; ethers such as anisole, trioxanone, diphenyl ether and diisopropyl ether; and mixtures of these solvents. Preferably, diphenyl ether is used as additional solvent.

The palladium can be present in the reaction mixture as a heterogeneous palladium compound or as a homogeneous palladium compound. However, homogeneous systems are preferred. Since palladium in situ forms a complex with the bidentate ligand, the choice of the initial Pd compound is in general not critical. Homogeneous palladium compounds include, for instance, palladium salts of, for instance, nitric acid, sulphonic acid, alkane carboxylic acids with not more than 12 carbon atoms or hydrogen halogenides (F, Cl, Br, I). Metallic palladium can also be used. Exemplary homogeneous palladium compounds include $PdCl_2$, $PdBr_2$, $PdI_2$, $Na_2PdI_4$, $K_2PdI_4$ $PdCl_2$ (benzonitrile)$_2$ and bis(allylpalladium chloride). Another group of suitable halogen-free palladium compounds are palladium complexes such as palladium acetylacetonate (Pd(acac)$_2$), Pd(II) acetate, Pd(NO$_3$)$_2$, o-tolyl phosphine palladium, and palladium (benzylidene acetone)$_2$. An exemplary of a heterogeneous palladium compound is a palladium compound on an ion exchanger such as, for example an ion exchanger containing carboxylic acid groups. Ion exchangers containing carboxylic acid groups are commercially available under the brand names Amberlite IRC 50 and Amberlite IRC 84 (Rohm & Haas). Another heterogeneous catalyst is an immobilized phosphine on carrier catalyst, in which the palladium forms a complex with the immobilized phosphine (phosphine being the ligand of the catalyst system). Carriers include polystyrene, polyacrylamide, or silica.

The palladium concentration in the reaction mixture is preferably as high as possible because the greater will be the rate of reaction per unit of reactor volume. The upper limit for a homogeneous catalyst system will normally be determined by the solubility of palladium in the reaction mixture and will, for example, depend on the specific palladium compound used as discussed above. This upper limit can easily be determined by one skilled in the art. However, the process according to the invention may also be performed with a homogeneous catalyst system in the presence of solid palladium compounds.

The pentenoate ester which is formed during carbonylation of butadiene will actually be a mixture of 2-, 3- and 4-pentenoate esters. The pentenoic acid used in the process according to the invention can also be 2-, 3- or 4-pentenoic acid or mixtures of any two or three of these isomeric pentenoic acids. The 2- and 3-pentenoic acids and esters are present in their cis and trans configuration.

The molar ratio of pentenoic acid to palladium is preferably greater than 10:1 and more preferably is greater than 20:1. An upper limit theoretically does not exist. The pentenoic acid can serve as solvent in this reaction. In practice the upper limit will be determined by the choice of a practical palladium concentration. The palladium concentration is preferably as high as possible as explained above. It has been found that virtually none of the pentenoic acid is carbonylated in the process according to the invention.

The alcohol is, for example, an organic with 1 to 20 carbon atoms. The organic compound can be an aliphatic, cycloaliphatic or aromatic compound. These compounds include, for instance, phenol, cresol, tert-butyl catechol and cyclohexanol. By preference, the alcohol is an aliphatic alcohol in which the aliphatic group is a straight or branched chain alkyl group. By preference, the alkyl group has 1 to 6 carbon atoms. These aliphatic alcohols can be alkanols represented by the formula ROH of which methanol, ethanol, propanol, isopropanol, butanol, tert-butanol, pentanol and hexanol are exemplary. Most preferably methanol or ethanol is used as the alcohol. Substituted alcohols can also be used such as, for instance, ether-substituted alcohols, of which the methyl ether of ethylene glycol is exemplary.

The molar ratio of alcohol to butadiene can vary between wide limits and generally lies between 10:1 and 1:10. Preferably the alcohol concentration in the reaction mixture is kept as low as possible while the amount of alcohol is at least the stoichiometric amount relative to butadiene. The low concentration of alcohol can be obtained by performing the carbonylation in the presence of large amounts of, for example, an additional solvent or (side-) products formed by the carbonylation reaction. The molar ratio of alcohol to butadiene is preferably at least 1:1, is preferably less than 3:1 and is more preferably less than 1.5:1.

The temperature of the carbonylation is preferably between 25° C. and 200° C. More preferably this temperature is between 80° C.–160° C. The pressure is not very critical and will generally be between 1 MPa and 100 MPa and preferably be between 2 MPa and 10 MPa.

The carbon monoxide can be used in a pure form or diluted with an inert gas such as, for example nitrogen, rare gases or carbon dioxide. In general more than 5% hydrogen is undesirable, since this can cause hydrogenation of butadiene under the carbonylation conditions. The amount of carbon monoxide is not critical if at least a stoichiometric amount of carbon monoxide relative to butadiene is supplied to the carbonylation reaction.

The carbonylation can be performed batch wise, semi-continuously or continuously. Preferably a continuous manner of operation is used in a commercial large scale process. When a monodentate phosphine ligand is used a continuous process is especially advantageous as explained above. By operating continuously fresh butadiene can be supplied to the catalyst system at a rate comparable to the rate of conversion of butadiene. Preferably alcohol is also supplied continuously to the catalyst system in a preferred ratio to butadiene as described above. In this manner a reasonable conversion of butadiene per mol palladium per hour and a high yield to pentenoate ester can be obtained. An example of such a mode of operation is a series of continuously stirred tank reactors (CSTR) in which the catalyst system, solvent, butadiene and alcohol are fed to the first reactor in the preferred ratios according to the process of the invention. Carbon monoxide is supplied to every reactor. The effluent of the first reactor is fed to the second reactor. Fresh butadiene and alcohol is also fed to the second reactor in the appropriate amounts and ratios. This procedure is repeated for the subsequent reactors. Instead of a series of CSTR's a tube reactor can, for example, be used in which butadiene and alcohol are supplied at intermediate locations along the tube.

The above described continuous process can also be advantageously used when performing the process with a catalyst system comprising multidentate phosphine ligands.

The invention is also directed to a continuous process of the preparation of pentenoate esters by carbonylation of butadiene or a butadiene derivative according to the process of the invention as described above wherein the following steps are performed;

(a) carbon monoxide, alkanol, the catalyst system and butadiene or a butadiene derivative are continuously fed to a reactor in which the carbonylation takes place, (b) separating from the effluent of the reactor unreacted carbon monoxide, unreacted butadiene and unreacted alcohol in one or more separation steps and returning these reactants to step (a) and isolating the pentenoate ester, (c) returning the remaining mixture of step (b), containing the catalyst system to step (a), (d) hydrolyzing part of the pentenoate ester in a separate step to pentenoic acid and returning the pentenoic acid to step (a).

Preferably a part of the remaining mixture of step (b) is separated from the mixture and led to a drain (purge) in order to prevent a build up of high boiling by-products in the circulating reaction mixture. In general, the purge stream will be reprocessed to retrieve, for example palladium and/or the phosphine ligand.

Step (a) can be performed in several ways such as, for example, in a continuously stirred tank reactor as described above or a bubble column in which the product is simultaneously stripped from the liquid phase.

Separating the carbon monoxide, butadiene, alcohol and the alkyl pentenoate from the reaction mixture in step (c) can be performed in various ways. Generally the carbon monoxide is separated first from the reaction mixture in for example a simple gas-liquid separation unit. The butadiene, alcohol and the pentenoate ester can be separated from the reaction mixture in one step followed by isolating the pentenoate ester from butadiene and alcohol. Preferably the butadiene and alcohol are separated from the reaction mixture in a separate step followed by the isolation of the pentenoate ester from the remaining reaction mixture. Separation of the various compounds can be performed in various ways such as, for example by a simple flash operation or by distillation. The choice as to which unit operation is the most suitable will depend, for example, on the physical properties of the compounds to be separated.

The invention will be elucidated with the following non-limiting examples. The selectivity and conversion mentioned in the examples are defined as follows:

$$\text{convern} = \frac{\text{converted butadiene (mol)}}{\text{initial amount of butadiene (mol)}} * 100\%$$

$$\frac{\text{selectivity of}}{\text{pentenoate}} = \frac{\text{obtained amount of pentenoate (mol)}}{\text{converted amount of butadiene (mol)}} * 100\%$$

In the above conversion and selectivity determinations, the term converted butadiene means the amount of butadiene which is reacted to (by)products which cannot react under the carbonylation reaction conditions in any way to the product 2-, 3- and 4-pentenoate). These (by)products are for example, butene, vinylcyclohexene and high boiling products, for example, $C_9$-heavies (e.g. nonadienoates) and higher boiling products. Excluded from this list are intermediates which can react to pentenoate.

Example I

A 50 ml Parr autoclave, made of Hastelloy C, was filled successively with 0.124 g (0.552 mmol) of Pd(II) acetate, 0.957 g (2.242 mmol) of 1,4-bis(diphenyl-phosphino)butane, 0.784 g (7.84 mmol) of 3-pentenoic acid and 10.13 g of diphenyl ether as a solvent. The autoclave was closed and purged three times with 4.0 MPa carbon monoxide. Subsequently, under a pressure of 1.0 MPa of CO while stirring at a speed of 1250 rpm, a mixture of 3.65 g (114 mmol) of methanol, 5.805 g (108 mmol) of butadiene and 0.480 g of nonane (internal standard for GC product analysis) was injected under pressure from an injection vessel into the autoclave. The temperature of the reaction mixture was raised to 140° C. at a CO pressure of 6.0 MPa. After 2.0 hours the reaction was stopped and the butadiene and the reaction products were analyzed by gas chromatographic methods.

The conversion was 75%. Selectivity to methyl pentenoates was 79%, and the activity was 58 $hr^{-1}$. 46% of the 3-pentenoic acid was converted to its methyl ester.

Comparative Experiment A

Example I was repeated using 2,4,6-trimethyl benzoic acid instead of 3-pentenoic acid, in 7 molar equivalents per Pd. After 3.8 hours the reaction was stopped.

The conversion was 86%. Selectivity to methyl pentenoates was 87%, and the activity was 39 $hr^{-1}$. 23% of the trimethyl benzoic acid was converted into its methyl ester.

Example II

A 150 ml Parr autoclave, made of Hastelloy C. was filled successively with 0.387 g (1.73 mmol) of Pd(II) acetate, 2.86 g (6.70 mmol) of 1,4-bis(diphenyl-phosphino)butane, 1.20 g (12 mmol) of 3-pentenoic acid, and 0.56 g of nonane (internal standard for GC product analysis) and 32.40 g of diphenyl ether as a solvent. The autoclave was closed and purged three times with 4.0 MPa carbon monoxide. Subsequently the temperature of the reaction mixture was raised to 140° C. at a CO pressure of 5.0 MPa, after which the butadiene, methanol and 3-pentenoic acid supplies were started at constant rates of 130, 171 and 7.8 mmol per hour respectively, using Gilson model 302 pumps. After 2.8 hours the reaction was stopped and the butadiene and the reaction products analyzed by gas chromatographic methods.

The conversion was 79%, and the selectivity to methyl pentenoates was 82%. The activity was 50 $hr^{-1}$, and 70% of the 3-pentenoic acid was converted to its methyl ester.

Example III

Example II was repeated, using triphenylphosphine as the ligand at a concentration of 10 equivalents per Pd, and adding 10 equivalents of 3-pentenoic acid prior to butadiene and methanol supply at rates of 40 and 48 mole/mole Pd/hr respectively. Together with methanol 4 equivalents of 3-pentenoic acid per palladium per hour were fed to the autoclave. After 5 hours the reaction was stopped.

The conversion was 81%, and the selectivity to methyl pentenoates was 88%. The activity was 29 hr$^{-1}$. 44% of the total amount of 3-pentenoic acid was converted to methyl-3-pentenoate.

Comparative Experiment B

A 50 ml Parr autoclave, made of Hastelloy C, was filled successively with 0.05 g (0.22 mmol) of Pd(II) acetate, 0.61 g (2.32 mmol) of triphenyl phosphine, 0.26 g (1.6 mmol) of 2,4,6-trimethyl benzoic acid and 27.0 g of diphenyl ether as a solvent. The autoclave was closed and purged three times with 4.0 MPa carbon monoxide. Subsequently, under a pressure of 1.0 MPa of CO, while stirring at a speed of 1250 rpm, a mixture of 3.76 g (118 mmol) of methanol, 5.14 g (95.3 mmol) of butadiene and 0.45 g of nonane (internal standard for GC product analysis) was injected under pressure from an injection vessel into the autoclave. The temperature of the reaction mixture was raised to 150° C. at a CO pressure of 6.0 MPa. After 5.0 hours the reaction was stopped and the butadiene and the reaction products were analyzed by gas chromatographic methods.

The conversion was 85%. Selectivity to methyl pentenoates was 21%, and the activity was 16 (hr$^{-1}$). 9% of the trimethyl benzoic acid was converted to its methyl ester.

Example IV

A 150 ml Parr autoclave, made of Hastelloy C, was filled successively with 0.43 g (1.94 mmol) palladium acetate, 5.0 g (19 mmol) triphenyl phosphine, 8.5 g (85 mmol) 3-pentenoic acid and 0.80 g nonane (internal standard for GC analysis). The autoclave was closed and purged three times with 4.0 MPa carbon monoxide. Subsequently the temperature of the reaction mixture was raised to 140° C. at a CO pressure of 4.0 MPa, and thereafter butadiene was supplied at 83 mmol per hour, and methanol at 83 mmol per hour. After one hour, 2.3 g (126 mmol) of water was injected into the autoclave under pressure. The pressure was raised to 6.0 MPa, and the butadiene and methanol supply continued at the same rates as during the first hour. After an additional two hours the reaction was stopped, and the contents of the autoclave were analyzed by gas-chromatographic methods.

The conversion was 80%. Selectivity to methyl pentenoates was 82%. Only 5% of 3-pentenoic acid was converted to methyl-3-pentenoate.

Example V

Example IV was repeated, except that water was continuously supplied together with methanol, at rates of 54 and 78 mmol per hour respectively. The butadiene supply was 78 mmol per hour. After four hours the reaction was stopped.

The conversion was 75% and the selectivity to methyl pentenoates 79%. No esterification of 3-pentenoic acid was observed.

What we claim is:

1. A process for the preparation of a pentenoate ester by carbonylation of butadiene or a butadiene derivative in the presence of carbon monoxide, alcohol and a catalyst system comprising palladium, a carboxylic acid and a phosphine ligand, wherein the carboxylic acid is pentenoic acid.

2. A process according to claim 1, wherein the molar ratio of pentenoic acid to palladium is greater than 10:1.

3. A process according to claims 1 wherein the molar ratio of alcohol to butadiene or butadiene derivative is between 1:1 and 3:1.

4. A process according to claim 1 wherein the alcohol is methanol or ethanol.

5. A process according to claim 1 wherein a part of the pentenoic ester is hydrolyzed to pentenoic acid, and the thus obtained pentenoic acid is recycled to the carbonylation reaction.

6. A process according to claim 1 wherein an amount of water is present during the carbonylation in an amount sufficient to maintain a catalytically active level of pentenoic acid.

7. A process according to claim 2, wherein the phosphine ligand is a monodentate phosphine ligand, the carbonylation is performed continuously or semi-continuously, and the amounts of the reactants are substantially maintained during the carbonylation such that the molar ratio of butadiene or butadiene derivative to palladium is less than 20:1, and the molar ratio of alcohol to butadiene or butadiene derivate is less than 2:1.

8. A process according to claims 1, 2 or 7, wherein the carboxylic acid present is the pentenoic acid.

9. A process for preparing a pentenoate ester comprising conducting the carbonylation of at least one member selected from the group consisting of butadiene and a butadiene derivative in a reaction mixture in the presence of carbon monoxide, an alcohol selected from the group consisting of methanol and ethanol, and a catalyst system, wherein said catalyst system is the combination palladium, a phosphine ligand, and pentenoic acid, wherein in said carbonylation the molar ratio of pentenoic acid to palladium is greater than 10:1, the molar ratio of said alcohol to butadiene or butadiene derivative is between 1:1 and 3:1.

\* \* \* \* \*

UNITED STATES PATENT AND TRADEMARK OFFICE
CERTIFICATE OF CORRECTION

PATENT NO. : 5,495,041

DATED : February 27, 1996

INVENTOR(S) : SIELCKEN et al.

It is certified that error appears in the above-indentified patent and that said Letters Patent is hereby corrected as shown below:

Column 4, line 11, please change "R" to --$R^5$--.

Signed and Sealed this

Twenty-seventh Day of May, 1997

Attest:

BRUCE LEHMAN

Attesting Officer     Commissioner of Patents and Trademarks